United States Patent
Sako et al.

(10) Patent No.: US 6,284,230 B1
(45) Date of Patent: *Sep. 4, 2001

(54) HAIR CONDITIONING SHAMPOO COMPOSITIONS COMPRISING PRIMARY ANIONIC SURFACTANT

(75) Inventors: Takashi Sako, Sumiyoshihommachi; Hirotaka Uchiyama, Nishiokamoto; Kiroh Harada, Uozaki Nakamachi; Fang Hu, Ashiya, all of (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/331,988
(22) PCT Filed: Dec. 30, 1996
(86) PCT No.: PCT/US96/20822
  § 371 Date: Jun. 30, 1999
  § 102(e) Date: Jun. 30, 1999
(87) PCT Pub. No.: WO98/29094
  PCT Pub. Date: Jul. 9, 1998
(51) Int. Cl.[7] ................. A61K 7/06; A61K 7/08
(52) U.S. Cl. .......... 424/70.11; 424/70.1; 424/70.12; 424/70.21; 424/70.22; 424/70.24; 424/70.27; 510/119
(58) Field of Search ............... 424/70.12, 70.1, 424/70.11, 70.22, 70.24, 70.27, 70.21; 510/119

(56) References Cited

U.S. PATENT DOCUMENTS 5,853,707 * 12/1998 Wells et al. .
5,955,066 * 9/1999 Sako et al. .

FOREIGN PATENT DOCUMENTS

| 4025424 A1 | 2/1992 | (DE) . | |
| 6-016534 | 7/1992 | (JP) | A61K/7/50 |
| 95/01152 | 1/1995 | (WO) | A61K/7/06 |
| 96/29049 | 9/1996 | (WO) | A61K/7/48 |

OTHER PUBLICATIONS

Chemical Abstracts, vol. 121, AN=17725, (JP 6016534 A (Shiseido Co.)).

* cited by examiner

*Primary Examiner*—Thurman K. Page
*Assistant Examiner*—Brian K. Seidleck
(74) *Attorney, Agent, or Firm*—Andrew A Paul; Stephen T. Murphy; Brent M. Peebles

(57) ABSTRACT

Hair conditioning shampoo compositions comprise (a) from about 0.05% to about 50% by weight of a primary anionic surfactant selected from the group consisting of polyhydrophilic anionic surfactants comprising at least one carboxy group and at least two hydrophilic groups, amino acid anionic surfactants, and salts and mixtures thereof; (b) from about 0.001M to about 0.5M of a polyvalent metal cation; (c) from about 0.05% to about 20% by weight of a cationic conditioning agent selected from the group consisting of cationic surfactant, cationic polymer, and mixtures thereof; (d) an additional detersive anionic surfactant comprising alkyl sulfate or alkyl ether sulfate; and (e) an aqueous carrier wherein components (a), (b), (c) and (d) are capable of forming a coacervate.

11 Claims, No Drawings

HAIR CONDITIONING SHAMPOO COMPOSITIONS COMPRISING PRIMARY ANIONIC SURFACTANT

This application is a 371 of PCT/US96/20822 filed Dec. 30, 1996.

TECHNICAL FIELD

The present invention relates to conditioning shampoo compositions which both cleanse the hair and condition the hair.

BACKGROUND

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair."

A variety of approaches have been developed to alleviate these after-shampoo problems. These approaches range from post-shampoo application of hair conditioners such as leave-on and rinse-off products, to hair conditioning shampoos which attempt to both cleanse and condition the hair from a single product. Hair conditioners are typically applied in a separate step following shampooing. The hair conditioners are either rinsed-off or left-on, depending upon the type. Of product used. Hair conditioners, however, have the disadvantage of requiring a separate and inconvenient treatment step. Conditioning shampoos, i.e. shampoos which both cleanse and condition the hair, are highly desirable products because they are convenient for consumers to use.

In order to provide hair conditioning benefits in a cleansing shampoo base, a wide variety of conditioning actives have been proposed. However, many of these actives have the disadvantage of leaving the hair feeling soiled or coated, of interfering with the cleansing efficacy of the shampoo.

Japanese Patent Laid-open (Kokai) H6-17097 published Jan. 25, 1994 discloses cleaning compositions such as shampoos comprising a polyvalent metal salt of anionic surfactant and a silicone derivative. Exemplified anionic surfactants include acyl amino acid salts. International Publication No. WO95/01152 published Jan. 12, 1995 discloses a hair conditioning shampoo comprising a detersive surfactant, a nonvolatile hair conditioning agent, and polyvalent metal cations in free ion form. Japanese Patent Laid-open (Kokai) H7-11287 published Jan. 13, 1995 discloses a cleaning composition such as shampoos comprising an N-acyl neutral amino acid magnesium salt and an anionic surfactant. Exemplified amino acid moieties of the magnesium salt are N-methyl-β-alanine and sarcosine.

In the present invention, a hair conditioning shampoo composition comprising a primary anionic surfactant, a polyvalent metal cation and a cationic conditioning agent has been developed. This composition provides conditioning shampoo compositions which have improved overall conditioning benefits, improved lathering, and preferable viscosity.

SUMMARY

The present invention relates to a hair conditioning shampoo composition comprising:

(a) from about 0.05% to about 50% by weight of a primary anionic surfactant selected from the group consisting of polyhydrophilic anionic surfactants, amino acid surfactants, and mixtures thereof;

(b) from about 0.001M to about 0.5M of a polyvalent metal cation;

(c) from about 0.05% to about 20% by weight of a cationic conditioning agent selected from the group consisting of cationic surfactants, cationic polymers, and mixtures thereof; and (d) the remainder an aqueous carrier;

wherein components (a), (b) and (c) are capable of forming a coacervate.

Such compositions satisfy the need for a hair conditioning shampoo composition which has improved overall conditioning benefits, improved lathering, and preferable viscosity.

In further embodiments, the present invention relates to a hair conditioning shampoo composition further comprising an additional detersive surfactant capable of forming a coacervate with components (a), (b) and (c); preferably selected from the group consisting of a secondary anionic surfactant and an amphoteric surfactant. In further embodiments, the present invention relates to a hair-conditioning shampoo composition further comprising additional conditioning agents selected from the group consisting of fatty compounds, silicone compounds, hydrocarbons, and mixtures thereof.

DETAILED DESCRIPTION

All percentages herein are by weight of the compositions unless otherwise indicated. All ratios are weight ratios unless otherwise indicated. All percentages, ratios, and levels of ingredients referred to herein are by weight and are based on the actual amount of the ingredient, and do not include solvents, fillers, or other materials with which the ingredient may be combined as commercially available products, unless otherwise indicated.

The invention hereof can comprise, consist of, or consist essentially of the essential elements described herein as well as any of the preferred or optional ingredients also described herein.

All publications, patent applications, and issued patents mentioned herein are hereby incorporated in their entirety by reference.

Primary Anionic Surfactant

The present invention comprises from about 0.05 to about 50%, preferably from about 0.1 to about 30%, more preferably from about 0.5% to about 20% of a primary anionic surfactant selected from the group consisting of polyhydrophilic anionic surfactants, amino acid surfactants, and mixtures thereof. The primary anionic surfactant is capable of forming a coacervate with the below mentioned polyvalent metal cations and below mentioned cationic conditioning agents. Preferably, the primary anionic surfactant is a polyhydrophilic anionic surfactant.

Polyhydrophilic anionic surfactants are useful as the primary anionic surfactants herein. By "polyhydrophilic" herein, is meant a surfactant that has at least two hydrophilic groups which provide a hydrophilic nature and are capable of forming salts With a metal cation, particularly with polyvalent metal cations. Polyhydrophilic surfactants useful in the present invention herein are only those having at least two hydrophilic groups in the molecule, and is not intended to encompass those which only have one hydrophilic group. One molecule of the polyhydrophilic anionic surfactant herein may comprise the same hydrophilic groups, or different hydrophilic groups. Specifically, the polyhydrophilic anionic surfactants of the present invention comprise at least one group selected from the group consisting of carboxy, hydroxy, sulfate, sulfonate, and phosphate. Suitable polyhydrophilic anionic surfactants are those which comprise at least one of a carboxy, sulfate, or sulfonate group, more preferably those which comprise at least one carboxy group.

Nonlimiting examples of polyhydrophilic anionic surfactants include N-acyl-L-glutamates such as N-cocoyl-L-glutamate and, N-lauroyl-L-glutamate, laurimino diproprionate, N-acyl-L-aspartate, di-(N-lauroyl N-methyl taurate), polyoxyethylene laurylsulfosuccinate, disodium N-octadecylsulfosuccinate; disodium lauryl sulfosuccinate; diammonium lauryl sulfosuccinate; tetra sodium N-(1,2-dicarboxyethyl)-N-octadecylsulfosuccinate; the diamyl ester of sodium sulfosuccinic acid; the dihexyl ester of sodium sulfosuccinic acid; and the dioctyl ester of sodium sulfosuccinic acid, and 2-cocoalkyl N-carboxyethyl N-carboxyethoxyethyl imidazolinium betaine, lauroamphohydroxypropylsulfonate, cocoglyceryl ether salts, cocoglyceride sulfate, lauroyl isethionate, lauroamphoacetate, and those of the following formula:

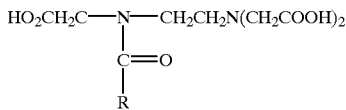

wherein R is an alkyl of 12 to 18 carbons. Other polyhydrophilic anionic surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The α-olefins from which the olefin sulfonates are derived are mono-olefins having about 12 to about 24 carbon atoms, preferably about 14 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A specific α-olefin sulfonate mixture of the above type is described more fully in U.S. Pat. No. 3,332,880, to Pflaumer and Kessler, issued Jul. 25, 1967, which is incorporated by reference herein in its entirety.

Another class of primary anionic surfactants are amino acid surfactants which are surfactants that have the basic chemical structure of an amino acid compound, i.e., that contains a structural component of one of the naturally-occurring amino acids. It is understood by the artisan that some surfactants may be regarded as both a polyhydrophilic anionic surfactant, and an amino acid surfactant. These surfactants are suitable primary anionic surfactants.

Nonlimiting examples of amino acid surfactants include, N-cocoylalaninate, N-acyl-N-methyl-β-alanate, N-acylsarcosinate; N-alkylamino propionates and N-alkyliminodipropionates, specific examples of which include N-lauryl-β-amino propionic acid or salts thereof, and N-lauryl-β-imino-dipropionate, N-acyl-DL-alaninate, sodium lauryl sarcosinate, sodium lauroyl sarcosinate, lauryl sarcosine, cocoyl sarcosine, N-acyl-N-methyl taurate, lauroyl taurate, and lauroyl lactylate.

Commercially available primary anionic surfactants suitable in the present invention are N-acyl-L-glutamate with a tradename AMISOFT CT-12S, N-acyl potassiumglycine with a tradename AMILITE GCK-12, lauroyl glutamate with a tradename AMISOFT LS-11, and N-acyl-DL-alaninate with tradename AMILITE ACT12 supplied by Ajinomoto; acylaspartate with tradenames ASPARACK and MS supplied by Mitsubishi Chemical; and acyl derivaties of tradename ED3A supplied by Hampshire Chemical Corp.

It has been found that these primary anionic surfactants, along with the cationic conditioning agents, and polyvalent metal cations as described later, form a coacervate in the compositions of the present invention.

Coacervate formulation is dependent upon a variety of criteria such as molecular weight, component concentration, and ratio of interacting ionic components ionic strength, charge density of the cationic and anionic components, pH, and temperature. Coacervate systems and the effect of these parameters are known in the art.

It is believed to be particularly advantageous, and to be the discovery of the present invention, for the primary anionic surfactants and the polyvalent metal cations at certain levels to be present with the cationic conditioning agents in a coacervate phase. The coacervates formed in the compositions of the present invention are believed to readily deposit on the hair upon diluting the coacervate with abundant water, i.e., rinsing of the shampoo.

Without being bound by theory, it is believed that the coacervates made by the essential components of the present invention provide two major effects to the present shampoo composition. First, it reduces the Critical Micelle Concentration (hereinafter "CMC") of the composition. The reduction of the CMC relates to reduction of the surface tension, thereby improving lather performance. Second, the existence of the primary anionic surfactants along with the polyvalent metal cations expand the coacervate region in the composition. As the cationic conditioning agents in the composition are mainly delivered to the hair via these coacervates, expansion of the coacervate region results in delivery of more cationic conditioning agents to the hair. Consequently, compositions which both cleanse and condition the hair from a single product, which have improved overall conditioning benefits and improved lathering are provided.

Techniques of analysis of formation of complex coacervates are known in the art. For example, microscopic analysis of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the shampoo composition.

Polyvalent Metal Cations

The present invention comprises a polyvalent metal cation at a level of from about 0.001M to about 0.5M, more preferably from about 0.05M to about 0.3M.

Suitable polyvalent metal cations include divalent and trivalent metals, divalent metals being preferred. Exemplary metal cations include alkaline earth metals, such as magnesium, calcium, zinc, and copper, and trivalent metals such as aluminum and iron. Preferred are calcium and magnesium.

The polyvalent metal cation can be added as an inorganic salt, organic salt, or as a hydroxide. The polyvalent metal cation may also be added as a salt with anionic surfactant, including the primary anionic surfactants as mentioned above, or detersive surfactants as mentioned below.

Preferably, the polyvalent metal cation is introduced as an inorganic salt or organic salt. Inorganic salts include chloride, bromide, iodine, nitrate, or sulfate, more preferably chloride or sulfate. Organic salts include L-glutamate, lactate, malate, succinate, acetate, fumarate, L-glutamic acid hydrochloride, and tartarate.

It will be clear to those skilled in the art that, if polyvalent salts of the anionic surfactant is used as the mode of introducing the polyvalent metal cations into the compositions hereof, only a fraction of the anionic surfactant may be of polyvalent form, the remainder of the anionic surfactant being necessarily added in monovalent form.

Hardness of the conditioning shampoo compositions can be measured by standard methods in the art, such as by ethylene diamine tetraacetic acid (EDTA) titration. In the event that the composition contains dyes or other color materials that interfere with the ability of EDTA titration to yield a perceptible color change, hardness should be determined for the composition in the absence of the interfering dye or color.

Cationic Conditioning Agent

The present invention comprises a cationic conditioning agent. The cationic conditioning agent are those which are capable of forming a coacervate in combination with the above mentioned primary anionic surfactants and polyvalent metal cations selected from the group consisting of cationic surfactants, cationic polymers, and mixtures thereof.

Cationic Surfactant

The cationic surfactants useful herein are any known to the artisan.

Among the cationic surfactants useful herein are those corresponding to the general formula (1):

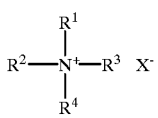

(I)

wherein at least one of $R^1$, $R^2$, $R^3$, and $R^4$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^1$, $R^2$, $R^3$, and $R^4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^1$, $R^2$, $R^3$, and $R^4$ are independently selected from $C_1$ to about $C_{22}$ alkyl. Nonlimiting examples of cationic surfactants useful in the present invention include the materials having the following CTFA designations: quaternium-8, quaternium-24, quaternium-26, quaternium-27, quaternium-30, quaternium-33, quaternium-43, quaternium-52, quaternium-53, quaternium-56, quaternium-60, quaternium-62, quaternium-70, quaternium-72, quaternium-75, quaternium-77, quaternium-78, quaternium-80, quaternium-81, quaternium-82, quaternium-83, quaternium-84, and mixtures thereof.

Also preferred are hydrophilically substituted cationic surfactants in which at least one of the substituents contain one or more aromatic, ether, ester, amido, or amino moieties present as substituents or as linkages in the radical chain, wherein at least one of the $R^1$–$R^4$ radicals contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Preferred hydrophilically substituted cationic surfactants include those of the formula (II) through (VII)

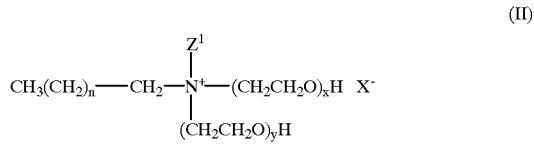

(II)

wherein n is from 8 to about 28, x+y is from 2 to about 40, $Z^1$ is a short chain alkyl, preferably a $C_1$–$C_3$ alkyl, more preferably methyl, or —$(CH_2CH_2O)_zH$ wherein x+y+z is up to 60, and X is a salt forming anion as defined above;

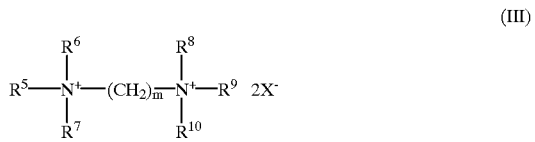

(III)

wherein m is 1 to 5, one or more of $R^5$, $R^6$, and $R^7$ are independently an $C_1$–$C_{30}$ alkyl, the remainder are —$CH_2CH_2OH$, one or two of $R^8$, $R^9$, and $R^{10}$ are independently an $C_1$–$C_{30}$ alkyl, and remainder are —$CH_2CH_2OH$, and X is a salt forming anion as mentioned above;

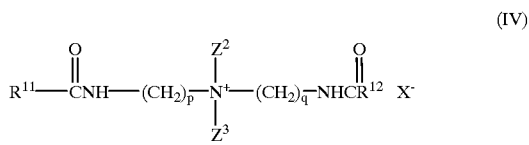

(IV)

wherein $Z^2$ is an alkyl, preferably a $C_1$–$C_3$ alkyl, more preferably methyl, and $Z^3$ is a short chain hydroxyalkyl, preferably hydroxymethyl or hydroxyethyl, p and q independently are integers from 2 to 4, inclusive, preferably from 2 to 3, inclusive, more preferably 2, $R^{11}$ and $R^{12}$, independently, are substituted or unsubstituted hydrocarbyls, preferably $C_{12}$–$C_{20}$ alkyl or alkenyl, and X is a salt forming anion as defined above;

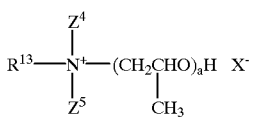

(V)

wherein $R^{13}$ is a hydrocarbyl, preferably a $C_1$–$C_3$ alkyl, more preferably methyl, $Z^4$ and $Z^5$ are, independently, short chain hydrocarbyls, preferably C2–C4 alkyl or alkenyl, more preferably ethyl, a is from 2 to about 40, preferably from about 7 to about 30, and X is a salt forming anion as defined above;

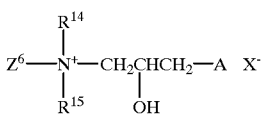

(VI)

wherein $R^{14}$ and $R^{15}$, independently, are $C_1$–$C_3$ alkyl, preferably methyl, $Z^6$ is a $C_{12}$–$C_{22}$ hydrocarbyl, alkyl carboxy or alkylamido, and A is a protein, preferably a collagen, keratin, milk protein, silk, soy protein, wheat protein, or hydrolyzed forms thereof; and X is a salt forming anion as defined above;

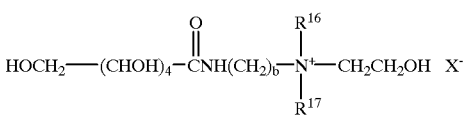

(VII)

wherein b is 2 or 3, $R^{16}$ and $R^{17}$, independently are $C_1$–$C_3$ hydrocarbyls preferably methyl, and X is a salt forming anion as defined above. Nonlimiting examples of hydrophilically substituted cationic surfactants useful in the present invention include the materials having the following CTFA designations: quaternium-16, quaternium61, quaternium-71, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein. Highly preferred compounds include commercially available materials of the following tradenames; VARIQUAT K1215 and 638 from Witco Chemical, MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel, and ATLAS G265 from ICI Americas.

Salts of primary, secondary, and tertiary fatty amines are also suitable cationic surfactants. The alkyl groups of such amines preferably have from about 12 to about 22 carbon atoms, and can be substituted or unsubstituted. Particularly useful are amido substituted tertiary fatty amines. Such amines, useful herein, include stearamidopropyidimethylamine, stearamidopropyldiethylamine, stearamidoethyidiethylamine, stearamidoethyidimethylamine, paimitamidopropyldimethylamine, paimitamidopropyidiethylamine, palmitamidoethyidiethylamine, palmitamidoethyldimethylamine, behenamidopropyldimethylamine, behenamidopropyldiethylamine, behenamidoethyidiethylamine, behenamidoethyldimethylamine, arachidamidopropyldimethylamine, arachidamidopropyidiethylamine, arachidamidoethyidiethylamine, arachidamidoethyldimethylamine, diethylaminoethylstearamide. Also useful are dimethylstearamine, dimethylsoyamine, soyamine, myristylamine, tridecylamine, ethyistearylamine, N-tallowpropane diamine, ethoxylated (with 5 moles of ethylene oxide) stearylamine, dihydroxyethylstearylamine, and arachidylbehenylamine. These amines can also be used in combination with acids such as L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055, Nachtigal, et al., issued Jun. 23, 1981, which is incorporated by reference herein in its entirety.

The cationic surfactants for use herein may also include a plurality of ammonium quaternary moieties or amino moieties, or a mixture thereof.

Cationic Polymers

The hair conditioning compositions of the present invention can further comprise one or more cationic polymer as a cationic conditioning agent. As used herein, the term "polymer" shall include materials whether made by polymerization of one type of monomer or made by two (i.e., copolymers) or more types of monomers.

Preferably, the cationic polymer is a water-soluble cationic polymer. By "water soluble" cationic polymer, what is meant is a polymer which is sufficiently soluble in water to form a substantially clear solution to the naked eye at a concentration of 0.1% in water (distilled or equivalent) at 25° C. The preferred polymer will be sufficiently soluble to form a substantially clear solution at 0.5% concentration, more preferably at 1.0% concentration.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density is preferably at least about 0.1 meq/gram, more preferably at least about 1.5 meq/gram, even more preferably at least about 1.1 meq/gram, still more preferably at least about 1.2 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaterniumn 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

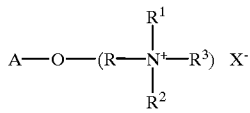

wherein: A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200®.

Other cationic polymers that can be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated herein by reference), and copolymers of etherified cellulose and starch (e.g., as described in U.S. Pat. No. 3,958,581, incorporated herein by reference.)

Aqueous Carrier

The compositions of the present invention comprise an aqueous carrier. The level and species of the carrier are selected according to the compatibility with other components to provide a coacervate, and other desired characteristic of the product.

The carrier useful in the present invention include water and solutions of lower alkyl alcohols, polyhydric alcohols. The lower alkyl alcohol useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Generally, the compositions of the present invention comprise from about 20% to about 95%, preferably from about 30% to about 92%, and more preferably from about 50% to about 90% water.

Additional Detersive Surfactant

The compositions of the present invention may further comprise an additional detersive surfactant selected from the group consisting of secondary anionic surfactants, amphoteric surfactants, zwitterionic surfactants, nonionic surfactants, and mixtures thereof. The additional detersive surfactant of the present invention is capable of forming a coacervate with the primary anionic surfactant, polyvalent metal cation, and cationic conditioning agents. The level and species of the additional detersive surfactant are selected according to the compatibility with other components, and desired characteristic of the product.

In preferred embodiments, the detersive surfactant comprises at least one secondary anionic surfactant, more preferably further comprises at least one amphoteric surfactant.

The purpose of a detersive surfactant is to provide cleansing performance to the composition. The term detersive surfactant, as used herein, is intended to distinguish these surfactants from surfactants which are primarily emulsifying surfactants, i.e. surfactants which provide an emulsifying benefit and which have low cleansing performance. It is recognized that most surfactants have both detersive and emulsifying properties. It is not intended to exclude emulsifying surfactants from the present invention, provided the surfactant also possesses sufficient detersive properties to be useful herein.

The additional detersive surfactant will be comprised at a level so that the total of additional detersive surfactant and primary anionic surfactant are from about 5% to about 75%, preferably from about 8% to about 50%, and more preferably from about 10% to about 30%, by weight of the composition.

Secondary Anionic Surfactants

Anionic surfactants useful herein include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to about 10, and M is hydrogen or a cation such as ammonium, alkanolammonium (e.g., triethanoiammonium), a monovalent metal cation (e.g., sodium and potassium), or a polyvalent metal cation (e.g., magnesium and calcium). Preferably, M should be chosen such that the anionic surfactant component is water soluble. The anionic surfactant or surfactants should be chosen such that the Krafft temperature is about 15° C. or less, preferably about 10° C. or less, and more preferably about 0° C. or less. It is also preferred that the anionic surfactant be soluble in the composition hereof.

Krafft temperature refers to the point at which solubility of an ionic surfactant becomes determined by crystal lattice energy and heat of hydration, and corresponds to a point at which solubility undergoes a sharp, discontinuous increase with increasing temperature. Each type of surfactant will have its own characteristic Krafft temperature. Krafft temperature for ionic surfactants is, in general, well known and understood in the art. See, for example, Myers, Drew, Surfactant Science and Technology, pp. 82–85, VCH Publishers, Inc. (New York, N.Y., USA), 1988 (ISBN 0-89573-399-0), which is incorporated by reference herein in its entirety.

In the alkyl and alkyl ether sulfates described above, preferably R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm oil, tallow, or the like, or the alcohols can be synthetic. Lauryl alcohol and straight chain alcohols derived from coconut oil and palm oil are preferred herein. Such alcohols are reacted with 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which can be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from 1 to about 4 moles of ethylene oxide. Such a mixture also comprises from 0% to about 20% by weight $C_{12-13}$ compounds; from about 60% to about 100% by weight of $C_{14-15-16}$ compounds, from 0% to about 20% by weight of $C_{17-18-19}$ compounds; from about 3% to about 30% by weight of compounds having a degree of ethoxylation of 0; from about 45% to about 90% by weight of compounds having a degree of ethoxylation of from 1 to about 4; from about 10% to about 25% by weight of compounds having a degree of ethoxylation of from about 4 to about 8; and from about 0.1% to about 15% by weight of compounds having a degree of ethoxylation greater than about 8.

Other suitable anionic surfactants are the water-soluble salts of organic, sulfuric acid reaction products of the general formula $[R^1\text{-}SO_3\text{-}M]$ where $R^1$ is selected from the group consisting of a straight or branched chain, saturated aliphatic hydrocarbon radical having from about 8 to about 24, preferably about 10 to about 18, carbon atoms; and M is as previously described above in this section. Examples of such surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other suitable anionic surfactants are the reaction products of fatty acids esterified with is ethionic acid and neutralized with sodium hydroxide where, for example, the fatty acids are derived from coconut or palm oil; or sodium or potassium salts of fatty acid amides of methyl tauride in which the fatty acids, for example, are derived from coconut oil. Other similar anionic surfactants are described in U.S. Pat. Nos. 2,486,921, 2,486,922, and 2,396,278, which are incorporated by reference herein in their entirety.

Another class of anionic surfactants suitable for use in the shampoo compositions are the β-alkyloxy alkane sulfonates. These compounds have the following formula:

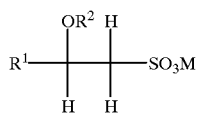

where $R^1$ is a straight chain alkyl group having from about 6 to about 20 carbon atoms, $R^2$ is a lower alkyl group having from about 1, preferred, to about 3 carbon atoms, and M is as hereinbefore described. Many other anionic surfactants suitable for use in the shampoo compositions are described in McCutcheon's, Emulsifiers and Detergents, 1989 Annual, published by M. C. Publishing Co., and in U.S. Pat. No. 3,929,678, which descriptions are incorporated herein by reference in their entirety. Preferred anionic surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate, and mixtures thereof.

Amphoteric and Zwitterionic Surfactants

The hair conditioning compositions of the present invention can comprise amphoteric and/or zwitterionic surfactants.

Amphoteric surfactants for use herein include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic surfactants for use herein include the derivatives of aliphatic quaternary ammonium, phosphonium, and sulfonium compounds, in which the aliphatic radicars are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

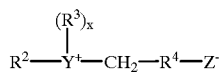

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom, and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines, including amidosultaines, include for example, cocodimethylpropylsultaine, stearyldimethylpropylsultaine, lauryl-bis-(2-hydroxyethyl)propylsultaine and the like; and the amidosultaines such as cocamidodimethylpropylsultaine, stearylamidododimethylpropylsultaine, laurylamido-bis-(2-hydroxyethyl)propylsultaine, and the like. Preferred are amidohydroxysultaines such as the $C_{12}$–$C_{18}$ hydrocarbylamidopropylhydroxysultaines, especially $C_{12}$–$C_{14}$ hydrocarbylamidopropylhydroxysultaines, e.g., laurylamidopropylhydroxysultaine and cocamidopropylhydroxysultaine. Other sultaines are described in U.S. Pat. No. 3,950,417, which is incorporated herein by reference in its entirety.

Other suitable amphoteric surfactants are the aminoalkanoates of the formula $RNH(CH_2)_nCOOM$, the iminodialkanoates of the formula $RN[(CH_2)_mCOOM]_2$ and mixtures thereof; wherein n and m are numbers from 1 to about 4, R is $C_8$–$C_{22}$ alkyl or alkenyl, and M is hydrogen, alkali metal, alkaline earth metal, ammonium or alkanolammonium.

Other suitable amphoteric surfactants include those represented by the formula:

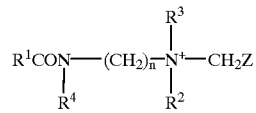

wherein $R^1$ is $C_8$–$C_{22}$ alkyl or alkenyl, preferably $C_{12}$–$C_{16}$, $R^2$ and $R^3$ is independently selected from the group consisting of hydrogen, —$CH_2CO_2M$, —$CH_2CH_2OH$, —$CH_2CH_2OCH_2CH_2COOM$, or —$(CH_2CH_2O)_mH$ wherein m is an integer from 1 to about 25, and $R^4$ is hydrogen, —$CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal (e.g., lithium, sodium, potassium), alkaline earth metal (beryllium, magnesium, calcium, strontium, barium), or ammonium. This type of surfactant is sometimes classified as an imidazoline-type amphoteric surfactant, although it should be recognized that it does not necessarily have to be derived, directly or indirectly, through an imidazoline intermediate. Suitable materials of this type are marketed under the tradename MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are monocarboxylates and di-carboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine surfactants, i.e. zwitterionic surfactants, suitable for use in the conditioning compositions are those represented by the formula:

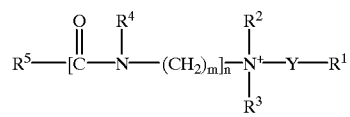

wherein: $R^1$ is a member selected from the group consisting of

COOM and $CH(OH)CH_2SO_3M$ $R^2$ is lower alkyl or hydroxyalkyl; $R^3$ is lower alkyl or hydroxyalkyl; $R^4$ is a member selected from the group consisting of hydrogen and lower alkyl; $R^5$ is higher alkyl or alkenyl; Y is lower alkyl, preferably methyl; m is an integer from 2 to 7, preferably from 2 to 3; n is the integer 1 or 0; M is hydrogen or a cation, as previously described, such as an alkali metal, alkaline earth metal, or ammonium. The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substituents such as hydroxyl or halogen radicals wherein the radical remains of hydrophobic character.

Examples of surfactant betaines of the above formula wherein n is zero which are useful herein include the alkylbetaines such as cocodimethylcarboxymethylbetaine, lauryldimethylcarboxymethylbetaine, lauryldimethyl-α-carboxyethylbetaine, cetyldimethylcarboxymethylbetaine, lauryl-bis-(2-hydroxyethyl)-carboxymethylbetaine, stearyl-bis-(2-hydroxypropyl)carboxymethylbetaine, oleyldimethyl-γ-carboxypropylbetaine, lauryl-bis-(2-hydroxypropyl)-α-carboxyethylbetaine, etc. The sulfobetaines may be represented by cocodimethylsulfopropylbetaine, stearyldimethylsulfopropylbetaine, lauryl-bis-(2-hydroxyethyl)-sulfopropylbetaine, and the like.

Specific examples of amido betaines and amidosulfobetaines useful in the conditioning compositions include the amidocarboxybetaines, such as cocamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocamido-bis-(2-hydroxyethyl)-carboxymethylbetaine, etc. The amidosulfobetaines may be represented by cocamidodimethylsulfopropylbetaine, stearylamidodimethylsulfopropylbetaine, laurylamido-bis-(2-hydroxyethyl)-sulfopropylbetaine, and the like.

Nonionic Surfactants

The shampoo compositions of the present invention can comprise a nonionic surfactant. Nonionic surfactants include those compounds produced by condensation of alkylene oxide groups, hydrophilic in nature, with an organic hydrophobic compound, which may be aliphatic or alkyl aromatic in nature.

Preferred nonlimiting examples of nonionic surfactants for use in the shampoo compositions include the following:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configurations, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) long chain tertiary amine oxides of the formula [$R^1 R^2 R^3 \rightarrow O$] where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula [RR'R"P→O] where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R" are each alkyl or monohydroxyalkyl groups containing from about 1 to about 3 carbon atoms;

(6) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties;

(7) alkyl polysaccharide (APS) surfactants (e.g. alkyl polyglycosides), examples of which are described in U.S. Pat. No. 4,565,647, which is incorporated herein by reference in its entirety, and which discloses APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside which is commercially available from Henkel, ICI Americas, and Seppic; and (8) polyoxyethylene alkyl ethers such as those of the formula $RO(CH_2CH_2)_nH$ and polyethylene glycol (PEG) glyceryl fatty esters, such as those of the formula $R(O)OCH_2CH(OH)CH_2(OCH_2CH_2)_nOH$, wherein n is from 1 to about 200, preferably from about 20 to about 100, and R is an alkyl having from about 8 to about 22 carbon atoms.

Additional Conditioning Agents

The compositions of the present invention may further comprise from about 0.05% to about 20%, preferably from about 0.1% to about 10%, and more preferably from about 0.5% to about 10% of additional hair conditioning agents selected from the group consisting of fatty compounds, silicone compounds, hydrocarbons, and mixtures thereof.

Fatty Compounds

Additional conditioning agents useful herein include fatty compounds selected from the group consisting of fatty alcohols, fatty acids, fatty alcohol derivatives, fatty acid derivatives, and mixtures thereof. The term fatty compounds is defined herein to include compounds selected from the group consisting of fatty alcohols, fatty acids, fatty alcohol derivatives, fatty acid derivatives, and also mixtures of one or more hereof. It is recognized that the compounds disclosed in this section of the specification can in some instances fall into more than one classification, e.g., some fatty alcohol derivatives can also be classified as fatty acid derivatives. Also, it is recognized that some of these compounds can have properties as nonionic surfactants and can alternatively be classified as such. However, a given classification is not intended to be a limitation on that particular compound, but is done so for convenience of classification and nomenclature. Nonlimiting examples of the fatty alcohols, fatty acids, fatty alcohol derivatives, and fatty acid derivatives are found in International Cosmetic Ingredient Dictionary, Fifth Edition, 1993, and CTFA Cosmetic Ingredient Handbook, Second Edition, 1992, both of which are incorporated by reference herein in their entirety.

The fatty alcohols useful herein are those having from about 10 to about 30 carbon atoms, preferably from about 12 to about 22 carbon atoms, and more preferably from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis-4-t-butylcyclohexanol, myricyl alcohol and mixtures thereof. Especially preferred fatty alcohols are those selected from the group consisting of cetyl alcohol, stearyl alcohol, isostearyl alcohol, oleyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and mixtures thereof. Especially preferred for use herein are the fatty acids selected from the group consisting of palmitic acid, stearic acid, and mixtures thereof.

The fatty alcohol derivatives are defined herein to include alkyl ethers of fatty alcohols, alkoxylated fatty alcohols, alkyl ethers of alkoxylated fatty alcohols, esters of fatty alcohols and mixtures thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth45, which are ethylene glycol ethers of cetyl alcohol, wherein the numeric designation indicates the number of ethylene glycol moieties present; the steareth series of compounds such as steareth-1 through 100, which are ethylene glycol ethers of steareth alcohol, wherein the numeric designation indicates the number of ethylene glycol moieties present; ceteareth 1 through ceteareth-50, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$–$C_{30}$ alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG-8-ceteth-1, and PPG-10 cetyl ether; and mixtures of all of the foregoing compounds. Preferred for use herein are steareth-2, steareth4, ceteth-2, and mixtures thereof.

The fatty acid derivatives are defined herein to include fatty acid esters of the fatty alcohols as defined above in this section, fatty acid esters of the fatty alcohol derivatives as defined above in this section when such fatty alcohol derivatives have an esterifiable hydroxyl group, fatty acid esters of alcohols other than the fatty alcohols and the fatty alcohol derivatives described above in this section, hydroxy-substituted fatty acids, and mixtures thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ehtyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and mixtures thereof. Preferred for use herein are glycerol monostearate, 12-hydroxy stearic acid, and mixtures thereof.

Silicone Compounds

Additional conditioning agents useful herein include silicone compounds. The silicone compounds hereof can include volatile soluble or insoluble, or nonvolatile soluble or insoluble silicone conditioning agents. By soluble what is meant is that the silicone compound is miscible with the carrier of the composition so as to form part of the same phase. By insoluble what is meant is that the silicone forms a separate, discontinuous phase from the carrier, such as in the form of an emulsion or a suspension of droplets of the silicone.

The silicone compounds for use herein will preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test Method CTM0004, Jul. 20, 1970, which is incorporated by reference herein in its entirety. Silicone compound of high molecular weight may be made by emulsion polymerization. Suitable silicone fluids include polyalkyl siloxanes, polyaryl siloxanes, polyalkylaryl siloxanes, polyether siloxane copolymers, and mixtures thereof. Other nonvolatile silicone compounds having hair conditioning properties can also be used.

The silicone compounds herein also include polyalkyl or polyaryl siloxanes with the following structure (i)

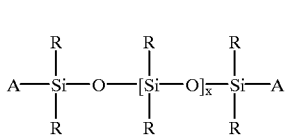

(I)

wherein R is alkyl or aryl, and x is an integer from about 7 to about 8,000. "A" represents groups which block the ends of the silicone chains. The alkyl or aryl groups substituted on the siloxane chain (R) or at the ends of the siloxane chains (A) can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable A groups include hydroxy, methyl, methoxy, ethoxy, propoxy, and aryloxy. The two R groups on the silicon atom may represent the same group or different groups. Preferably, the two R groups represent the same group. Suitable R groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their ViscasilR and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

The silicone compounds that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These material are also known as dimethicone copolyols.

Other silicone compounds include amino substituted materials. Suitable alkylamino substituted silicone compounds include those represented by the following structure (II)

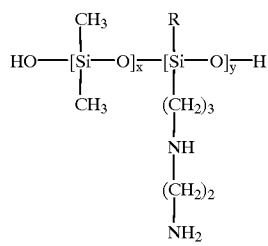

(II)

wherein R is $CH_3$ or OH, x and y are integers which depend on the molecular weight, the average molecular weight being approximately between 5,000 and 10,000. This polymer is also known as "amodimethicone".

Suitable amino substituted silicone fluids include those represented by the formula (III)

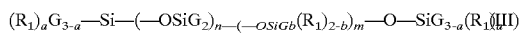

in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical of formula $CqH_{2q}L$ in which q is an integer from 2 to 8 and L is chosen from the groups

—$N(R_2)CH_2$—$CH_2$—$N(R_2)_2$

—$N(R_2)_2$

—$N(R_2)_3A^-$

—$N(R_2)CH_2$—$CH_2$—$NR_2H_2A^-$ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred amino substituted silicone corresponding to formula (III) is the polymer known as "trimethylsilylamodimethicone", of formula (IV):

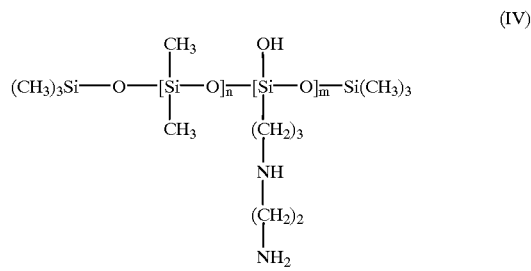

In this formula n and m are selected depending on the exact molecular weight of the compound desired.

Other amino substituted silicone polymers which can be used are represented by the formula (V):

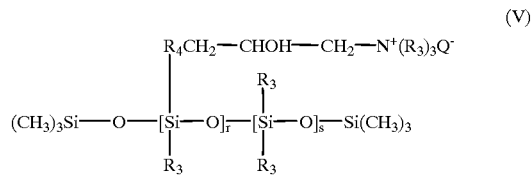

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

References disclosing suitable nonvolatile dispersed silicone compounds include U.S. Pat. No. 2,826,551, to Geen; U.S. Pat. No. 3,964,500, to Drakoff, issued Jun. 22, 1976; U.S. Pat. No. 4,364,837, to Pader; and British Pat. No. 849,433, to Woolston, all of which are incorporated herein by reference in their entirety. Also incorporated herein by reference in its entirety is "Silicon Compounds" distributed by Petrarch Systems, Inc., 1984. This reference provides an extensive, though not exclusive, listing of suitable silicone compounds.

Another nonvolatile dispersed silicone that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference in their entirety. The "silicone gums" will typically have a mass molecular weight in excess of about 200,000, generally between about 200,000 and about 1,000,000. Specific examples include polydimethylsiloxane, poly (dimethylsiloxane methylvinylsiloxane) copolymer, poly (dimethylsiloxane diphenylsiloxane methylvinylsiloxane) copolymer and mixtures thereof:

Also useful are silicone resins, which are highly crosslinked polymeric siloxane systems. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

The method of manufacturing these silicone compounds, can be found in Encyclopedia of Polymer Science and Engineering, Volume 15, Second Edition, pp 204–308, John Wiley & Sons, Inc., 1989, which is incorporated herein by reference in its entirety.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO)_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

Optional Components

In addition to the required components, the compositions herein can also contain a wide variety of optional components. Nonlimiting examples of these components are disclosed in International Cosmetic Ingredient Dictionary, Fifth Edition, 1993, and CTFA Cosmetic Ingredient Handbook, Second Edition, 1992, both of which are incorporated by reference herein in their entirety. Some nonlimiting examples of optional components are disclosed below.

Suspending Agents

A preferred optional component is a suspending agent, particularly for compositions comprising silicone compounds of high viscosity and/or large particle size. When present, the suspending agent is in dispersed form in the shampoo compositions. The suspending agent will generally comprise from about 0.1% to about 10%, and more typically from about 0.3% to about 5.0%, by weight, of the shampoo composition.

Preferred suspending agents include acyl derivatives such as ethylene glycol stearates, both mono and distearate, long chain amine oxides such as alkyl $(C_{16}-C_{22})$ dimethyl amine oxides, e.g., stearyl dimethyl amine oxide, and mixtures thereof. When used in the shampoo compositions, these preferred suspending agents are present in the composition in crystalline form. These suspending agents are described in U.S. Pat. No. 4,741,855.

Other suitable suspending agents include alkanol amides of fatty acids, preferably having from about 16 to about 22 carbon atoms, more preferably about 16 to 18 carbon atoms, preferred examples of which include stearic monoethanolamide, cocomonoethanolamide, stearic diethanolamide, stearic monoisopropanolamide and stearic monoethanolamide stearate.

Other suitable suspending agents include N,N-dihydrocarbyl amido benzoic acid and soluble salts thereof (e.g., Na and K salts), particularly N,N-di(hydrogenated) $C_{16}$, $C_{18}$ and tallow amido benzoic acid species of this family, which are commercially available from Stepan Company (Northfield, Ill., USA).

Other suitable suspending agents include xanthan gum. The use of xanthan gum as a suspending agent in silicone containing shampoo compositions is described, for example, in U.S. Pat. No. 4,788,006, which is incorporated herein by reference in its entirety. Combinations of long chain acyl derivatives and xanthan gum may also be used as a suspending agent in the shampoo compositions. Such combinations are described in U.S. Pat. 4,704,272, which is incorporated herein by reference in its entirety.

Other suitable suspending agents include carboxyvinyl polymers. Preferred among these polymers are the copolymers of acrylic acid crosslinked with polyallylsucrose as described in U.S. Pat. No. 2,798,053, which is incorporated herein by reference in its entirety. Examples of these polymers include the carbomers, which are hompolymers of acrylic acid crosslinked with an allyl ether of pentaerythrotol, an allyl ether of sucrose, or an allyl ether of propylene. Preferred carboxyvinyl polymers have a molecular weight of at least about 750,000; more preferred are carboxyvinyl polymers having a molecular weight of at least about 1,250,000; most preferred are carboxyvinyl polymers having a molecular weight of at least about 3,000,000.

Other suitable suspending agents can be used in the shampoo compositions, including those that can impart a gel-like viscosity to the composition, such as water soluble or colloidally water soluble polymers like cellulose ethers such as hydroxyethyl cellulose, and materials such as guar gum, polyvinyl alcohol, polyvinyl pyrrolidone, hydroxypropyl guar gum, starch and starch derivatives.

Polyalkylene Glycols

An optional component of the present invention is a polyalkylene glycol. These compounds are particularly useful for compositions which are designed to impart a soft, moist feeling to the hair. When present, the polyalkylene glycol is typically used at a level from about 0.025% to about 1.5%, preferably from about 0.05% to about 1%, and more preferably from about 0.1% to about 0.5% of the compositions of the present invention.

The polyalkylene glycols are characterized by the general formula:

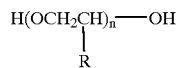

wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from about 1500 to about 25,000, preferably from about 2500 to about 20,000, and more preferably from about 3500 to about 15,000. Polyethylene glycol polymers useful herein are PEG-2M wherein R equals H and n has an average value of about 2,000 (PEG-2M is also known as Polyox WSR® N-10, which is available from Union Carbide and as PEG-2,000); PEG-5M wherein R equals H and n has an average value of about 5,000 (PEG-5M is also known as Polyox WSR® N-35 and Polyox WSR® N-80, both available from Union Carbide and as PEG-5,000 and Polyethylene Glycol 300,000); PEG-7M wherein R equals H and n has an average value of about 7,000 (PEG-7M is also known as Polyox WSR® N-750 available from Union Carbide); PEG-9M wherein R equals H and n has an average value of about 9,000 (PEG 9-M is also known as Polyox WSR® N-3333 available from Union Carbide); and PEG-14 M wherein R equals H and n has an average value of about 14,000 (PEG-14M is also known as Polyox WSR® N-3000 available from Union Carbide). Other useful polymers include the polypropylene glycols and mixed polyethylene/polypropylene glycols.

A wide variety of additional ingredients can be formulated into the present composition. These include: other conditioning agents such as hydrolysed collagen, hydrolysed keratin, proteins, plant extracts, and nutrients; hair-hold polymers; preservatives such as benzyl alcohol, methyl paraben, propyl paraben and imidazolidinyl urea; solvents such as polyvinyl alcohol, ethyl alcohol and volatile and non-volatile silicone fluids of low molecular weight; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; sequestering agents, such as disodium ethylenediamine tetra-acetate; and polymer plasticizing agents, such as glycerin, disobutyl adipate, butyl stearate, and propylene glycol; and ultraviolet and infrared screening and absorbing agents such as octyl salicylate. Such optional ingredients generally are used individually at levels from about 0.01% to about 10.0%, preferably from about 0.05% to about 5.0% by weight of the composition.

Method of Use

The conditioning shampoos of the present invention are used in a conventional manner for cleaning and conditioning the hair and/or scalp. An effective amount of the shampoo composition, typically from about 1 gram to about 50 grams, and preferably from about 1 gram to about 20 grams, is applied to the hair. Preferably the hair has been wetted with water before application of the shampoo. Application of the shampoo typically includes working the composition through the hair, generally with the hands and fingers, to generate a lather. The shampoo product is then typically rinsed from the hair with water. This method for cleaning and conditioning the hair comprises the steps of:

(a) wetting the hair with water, (b) applying an effective amount of the conditioning shampoo of the present invention to the hair, (c) shampoo the hair with the composition, i.e. working the composition in contact with the hair and into a lather, and (d) rinsing the conditioning shampoo from the hair using water.

These steps can be repeated as many times as desired to achieve the cleaning and conditioning benefit sought.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

Examples I through X as shown below can be prepared by any conventional method well known in the art. A suitable method is as follows: A silicone emulsion is made with Dimethicone or Dimethiconol, a small amount of detersive surfactant, and a portion of water. Separately, Polyquaternium-10, primary anionic surfactants, and remaining detersive surfactants are dispersed in remaining water to form a homogeneous mixture. To this mixture is added other ingredients except for silicone emulsion, perfume, and magnesium salt, and agitated. The obtained mixture is passed through a heat exchanger to cool, and the silicone emulsion, perfume, and magnesium salt is added. The obtained compositions are poured into bottles to make hair conditioning shampoo compositions.

The hair conditioning shampoo compositions of Examples I through X provide improved overall conditioning benefits, improved lathering, and preferable viscosity.

| Components | Example Number Percent By Weight | | | | |
|---|---|---|---|---|---|
| | I | II | III | IV | V |
| N-acyl-L-glutamate | 1.0 | 1.0 | 3.0 | 1.0 | 5.0 |
| Sodium Lauroyl Sarcosinate | 0 | 0 | 0 | 0 | 2.0 |
| $MgCl_2$ | 0.5 | 0.5 | 0.5 | 0.5 | 0.5 |
| Behenyl Trimethylammonium chloride | 0.5 | 0 | 0 | 0 | 0.5 |
| Polyquaternium-10 | 1.0 | 1.0 | 1.0 | 0.5 | 1.0 |
| Ammonium Laureth-3 Sulfate | 12.0 | 12.0 | 12.0 | 15.0 | 12.0 |
| Ammonium Lauryl Sulfate | 4.0 | 4.0 | 4.0 | 5.0 | 4.0 |
| Cocamidopropylbetaine | 0.5 | 0 | 0 | 0 | 0 |
| Dimethicone *[1] | 2.0 | 2.5 | 2.0 | 2.0 | 2.0 |
| Cetyl Alcohol | 0.7 | 0.7 | 1.0 | 0.7 | 0.7 |
| Stearyl Alcohol | 0.3 | 0.3 | 0 | 0.3 | 0.3 |
| Cocamide MEA | 0.7 | 0.9 | 0.7 | 0.9 | 0.7 |
| Ethylene Glycol Distearate | 1.6 | 2.0 | 1.6 | 2.0 | 1.6 |
| Fragrance | 0.5 | 0.5 | 0.5 | 0.5 | 0.5 |
| DMDM Hydantoin | 0.20 | 0.20 | 0.20 | 0.20 | 0.20 |
| Water | ----q.s. to 100%---- | | | | |

*[1] Dimethicone: Dimethylpolysiloxanes having a molecular weight of 200,000 to 600,000

| Component | Example Number Percent By Weight | | | | |
|---|---|---|---|---|---|
| | VI | VII | VIII | IX | X |
| Sodium Lauroyl Sarcosinate | 15.0 | 1.0 | 1.0 | 3.0 | 3.0 |
| $MgSO_4$ | 0.5 | 0.5 | 0.5 | 0.5 | 0.5 |
| Polyquaternium-10 | 1.0 | 1.0 | 1.0 | 1.0 | 1.0 |
| Ammonium Laureth-3 Sulfate | 0 | 12.0 | 12.0 | 12.0 | 12.0 |
| Ammonium Lauryl Sulfate | 0 | 4.0 | 4.0 | 4.0 | 4.0 |
| Dimethiconol *[2] | 2.0 | 2.5 | 2.0 | 2.0 | 2.0 |
| Cetyl Alcohol | 1.0 | 1.4 | 0.42 | 0.7 | 0.63 |
| Stearyl Alcohol | 0.5 | 0.6 | 0.18 | 0.3 | 0.27 |
| Steareth-2 | 0 | 0 | 0.9 | 0 | 0 |
| Cocamide MEA | 0.7 | 0.7 | 0.7 | 0.7 | 0.7 |
| Ethylene Glycol Distearate | 1.6 | 1.6 | 1.6 | 1.6 | 1.6 |
| Fragrance | 0.5 | 0.5 | 0.5 | 0.5 | 0.5 |
| DMDM Hydantoin | 0.20 | 0.20 | 0.20 | 0.20 | 0.20 |
| Water | ----q.s. to 100%---- | | | | |

*[2] Dimethiconol: Hydroxy terminated dimethylpolysiloxanes having a molecular weight of 150,000 to 300,000

What is claimed is:

1. A hair conditioning shampoo composition comprising:
(a) from about 0.05% to about 50% by weight of a primary anionic surfactant selected from the group consisting of polyhydrophilic anionic surfactants comprising at least one carboxy group and at least two hydrophilic groups, amino acid anionic surfactants, and salts and mixtures thereof;
(b) from about 0.001M to about 0.5M of a polyvalent metal cation;
(c) from about 0.05% to about 20% by weight of a cationic conditioning agent selected from the group consisting of cationic surfactant, cationic polymer, and mixtures thereof;
(d) an additional detersive anionic surfactant comprising alkyl sulfate or alkyl ether sulfate; and
(e) an aqueous carrier
wherein components (a), (b), (c) and (d) form a coaceriate in the composition.

2. The hair conditioning shampoo composition according to claim 1, wherein the polyvalent metal cation is incorporated in the composition as an inorganic salt.

3. The hair conditioning shampoo composition according to claim 2, comprising from about 0.05M to about 0.3M of a polyvalent metal cation.

4. The hair conditioning shampoo composition according to claim 3, further comprising at least one additional conditioning agent selected from the group consisting of fatty compounds, silicone compounds, hydrocarbons, and mixtures thereof.

5. The hair conditioning shampoo composition according to claim 1 wherein the polyhydrophilic anionic surfactant comprises N-acyl-L-glutamate, laurimino diproprionate, N-acyl-L-aspartate, di-(N-lauroyl N-methyl taurate), polyoxyethylene laurylsulfosuccinate, disodium N-octadecylsulfosuccinate, disodium lauryl sulfosuccinate, diammonium lauryl sulfosuccinate, tetra sodium N-(1,2-dicarboxyethyl)-N-octadecylsulfosuccinate, diamyl ester of sodium sulfosuccinic acid, dihexyl ester of sodium sulfosuccinic acid, dioctyl ester of sodium sulfosuccinic acid, cocoglyceryl ether salt, cocoglyceride sulfate, lauroyl isethionate, or those of the following formula:

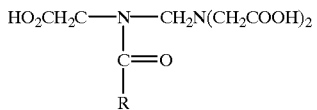

wherein R is an alkyl of 12 to 18 carbons.

6. The hair conditioning shampoo composition according to claim 1 wherein the amino acid anionic surfactant comprises N-cocoylalaninate, N-acyl-N-methyl-β-alanate, N-acylsarcosinate, N-alkylamino propionate, N-alkyliminodipropionate, N-acyl-DL-alaninate, sodium lauryl sarcosinate, sodium lauroyl sarcosinate, lauryl sarcosine, cocoyl sarcosine, N-acyl-N-methyl taurate, lauroyl taurate, or lauroyl lactylate.

7. The hair conditioning shampoo composition according to claim 1 wherein the amino acid anionic surfactant comprises N-acyl-L-glutamate, N-acyl potassiumglycine, N-lauryl-β-iminodipropionate, lauroyl glutamate, N-acyl-DL-alaninate, or acylaspartate.

8. The hair conditioning shampoo composition according to claim 1 further comprising a detersive amphoteric surfactant.

9. The hair conditioning shampoo composition of claim 1, wherein the primary anionic surfactant and the additional detersive anionic surfactant are present at a combined level of from about 5% to about 75% by weight of the composition.

10. The hair conditioning shampoo composition according to claim 8 wherein the amphoteric surfactant comprises the derivative of an aliphatic secondary or tertiary amine wherein one of the aliphatic substituents contains from about 8 to about 18 carbon atoms and one contains an anionic water solubilizing group comprising carboxy, sulfonate, sulfate, phosphate, or phosphonate.

11. The hair conditioning shampoo composition according to claim 8 wherein the zwitterionic surfactant comprises a derivative of aliphatic quaternary ammonium, phosphonium, or sulfonium compound wherein one of the aliphatic substituents contains from about 8 to about 18 carbon atoms and one contains an anionic group comprising carboxy, sulfonate, sulfate, phosphate, or phosphonate.

* * * * *